(12) United States Patent
Lambert et al.

(10) Patent No.: US 9,724,278 B2
(45) Date of Patent: Aug. 8, 2017

(54) ORAL COMPOSITIONS AND USES THEREOF

(75) Inventors: Pierre Lambert, Fleron (BE); Claude Blanvalet, Liege (BE)

(73) Assignee: Colgate-Palmolive Company, New York, NY (US)

( * ) Notice: Subject to any disclaimer, the term of this patent is extended or adjusted under 35 U.S.C. 154(b) by 2001 days.

(21) Appl. No.: 12/138,647

(22) Filed: Jun. 13, 2008

(65) Prior Publication Data

US 2009/0311200 A1 Dec. 17, 2009

(51) Int. Cl.
A61K 8/03 (2006.01)
A61K 8/34 (2006.01)
A61Q 11/00 (2006.01)

(52) U.S. Cl.
CPC .............. *A61K 8/03* (2013.01); *A61K 8/345* (2013.01); *A61Q 11/00* (2013.01)

(58) Field of Classification Search
CPC ...................................................... A61K 8/03
See application file for complete search history.

(56) References Cited

U.S. PATENT DOCUMENTS

| | | | |
|---|---|---|---|
| 3,696,191 A | 10/1972 | Weeks | |
| 3,697,220 A | 10/1972 | Schwartz | |
| 3,874,870 A | 4/1975 | Green et al. | |
| 3,991,177 A | 11/1976 | Vidra et al. | |
| 4,022,909 A | 5/1977 | Hunsucker | |
| 4,058,595 A | 11/1977 | Colodney | |
| 4,123,512 A | 10/1978 | Gaffar | |
| 4,125,603 A | 11/1978 | Audibert et al. | |
| 4,154,815 A | 5/1979 | Pader | |
| 4,343,730 A | 8/1982 | Becker et al. | |
| 4,347,238 A | 8/1982 | Hollingsbee | |
| 4,355,022 A | 10/1982 | Rabussay | |
| 4,442,125 A | 4/1984 | Thiele | |
| 4,525,342 A | 6/1985 | Weiss et al. | |
| 4,525,432 A | 6/1985 | Saito et al. | |
| 4,590,215 A | 5/1986 | Yamaguchi et al. | |
| 4,693,888 A | 9/1987 | Miyahara et al. | |
| 4,992,420 A | 2/1991 | Neeser | |
| 5,000,939 A | 3/1991 | Dring et al. | |
| 5,006,939 A | 4/1991 | Cawley | |
| 5,292,526 A | 3/1994 | Gaffar et al. | |
| 5,496,540 A * | 3/1996 | Gaffar et al. | ............ 424/49 |
| 5,942,211 A * | 8/1999 | Harper et al. | ............ 424/49 |
| 6,465,521 B1 | 10/2002 | Rosenberg | |
| 6,521,216 B1 | 2/2003 | Glandorf et al. | |
| 7,820,758 B1 * | 10/2010 | O'Lenick et al. | ........... 525/32.1 |
| 2002/0054859 A1 | 5/2002 | Alvarez Hernandez | |
| 2002/0068074 A1 | 6/2002 | Gandini et al. | |
| 2003/0152524 A1 | 8/2003 | Eshita | |
| 2004/0067203 A1 * | 4/2004 | Parikh | .............................. 424/49 |
| 2005/0002876 A1 * | 1/2005 | Yukl et al. | ...................... 424/54 |
| 2005/0210615 A1 * | 9/2005 | Shastry et al. | ............... 15/210.1 |
| 2005/0255072 A1 | 11/2005 | Jampani et al. | |

FOREIGN PATENT DOCUMENTS

| | | |
|---|---|---|
| AT | 377436 | 3/1985 |
| CA | 1334173 | 1/1995 |
| CA | 2302400 | 3/1999 |
| CA | 2302401 | 3/1999 |
| CA | 2327394 | 10/1999 |
| CA | 2370375 | 11/2000 |
| CN | 1990004 A | 7/2007 |
| DE | 3910170 | 10/1989 |
| EP | 1561454 | 8/2005 |
| EP | 1797860 | 6/2007 |
| GB | 641203 | 8/1950 |
| GB | 837068 | 6/1960 |
| GB | 1018454 | 1/1966 |
| GB | 1062895 | 3/1967 |
| GB | 1080994 | 8/1967 |
| GB | 1505069 | 3/1978 |
| GB | 2045241 | 10/1980 |
| GB | 2219937 | 12/1989 |
| IL | 85934 | 2/1992 |
| JP | 54-98344 | 8/1979 |
| JP | 61-151112 | 7/1986 |
| JP | 62-145016 | 6/1987 |
| JP | 63-060919 | 3/1988 |
| JP | 1-305022 | 12/1989 |
| JP | H11-79962 | 3/1999 |
| JP | 2003-231622 | 8/2003 |
| JP | 2004-517820 | 6/2004 |
| RU | 2116781 | 8/1998 |
| WO | WO 2007/076444 | 7/2007 |

OTHER PUBLICATIONS

Goldberg et al., 1991, "Bacterial Desorption by Commercial Mouthwashes vs. Two-Phase Oil: Water Formulations," Biofouling 3:193-198.

International Search Report and Written Opinion in International Application No. PCT/US09/047383 mailed Jun. 10, 2011.

(Continued)

*Primary Examiner* — Dennis J Parad

(57) ABSTRACT

The present invention is directed to a dual phase mouth wash composition comprising a hydrophilic phase, a hydrophobic phase, and a hydrotrope, and methods of use thereof. The hydrophilic and hydrophobic phases remain separated and form a temporary emulsion when mixed. The emulsion spontaneously reverts back to the two original phases after rest, without the formation of a emulsion.

20 Claims, No Drawings

(56) References Cited

OTHER PUBLICATIONS

Kjaerheim et al., 1995, "Experiments with Two-Phase Plaque-Inhibiting Mouthrinses," European J. Oral Science 103(3):179-181 (Abstract).
Weiss et al., 1982. "Cell-Surface Hydrophobicity of Adherent Oral Bacteria," Curt. Microbiol. 7:125-128.

\* cited by examiner

ORAL COMPOSITIONS AND USES THEREOF

BACKGROUND OF THE INVENTION

Dual phase mouth wash compositions are known in the art. U.S. Pat. No. 4,525,432 provides for mouth wash compositions which comprise an oily and aqueous phase, which are mixed just prior to their use. Preferably, such compositions are essentially detergent-free. As stated therein, the use of detergents in the oral cavity has an adverse effect, such as gum recession, circulatory impairment, hyperdydration of exposed tissue, edema, as well as allergic reactions. U.S. Pat. No. 6,465,521 provides for a dual phase mouth rinse which comprises an aqueous phase, a water immiscible oily phase, and a cationic surfactant from about 0.003 to about 2.0% weight to enable the formation of a temporary oil-in-water emulsion, wherein the emulsion breaks down and separates within a period of about 10 seconds to thirty minutes after the formation of the emulsion. However, it has been found that such compositions do not completely separate into oil and aqueous phases, and a thin emulsion may be observed between the oily and aqueous phases which persists for longer than 30 minutes. The thin emulsion may adhere to the container, which contains the composition, and remains adhered to the container even after subsequent mixing of the composition. The presence of the emulsion may be unattractive to users of the composition, as the presence of such emulsion might connote the presence of contaminants, successive "rings" of the emulsion remain adhered to the container after each use, or that the composition does not completely separate into aqueous and oily phases.

One of the benefits of a dual phase mouth wash composition is that the hydrophobic phase generally resides above the hydrophilic phase as the hydrophilic phase is generally more dense than the hydrophobic phase. Such a configuration is beneficial to the stability of actives that reside in the hydrophilic phase, as actives are commonly degraded by oxidation, e.g., when exposed to air. The separation of the hydrophobic phase on top of the hydrophilic phase essentially prevents or inhibits the oxidation of such actives. Thus, in compositions where the hydrophobic and hydrophilic phases do not completely separate, e.g., emulsion remains after allowing the composition to remain at rest, the actives in the hydrophilic phase are subject to degradation by oxidation. Thus, there is a need to develop oral care compositions comprising a hydrophilic and hydrophobic phase which separates into two distinct phases, and does not contain a microemulsion created by mixing the phases together.

BRIEF SUMMARY OF THE INVENTION

It has been surprisingly discovered that the use of particular coupling agents in a dual phase mouth wash forms a temporarily stable microemulsion when a dual phase mouth wash is mixed. The microemulsion is not readily observable by the user of the composition, and enables the delivery of actives present in either of the two phases to the oral cavity. The microemulsion separates back into hydrophobic and hydrophilic phases when let at rest, e.g., within two minutes from formation of the microemulsion by mixing.

The present invention is directed in part to mouth wash having at least two phases. e.g., a hydrophilic phase and a hydrophobic phase. The hydrophilic and hydrophobic phases remain separated while at rest; however, upon shaking generates a dispersion of the hydrophobic phase in the hydrophilic phase, e.g., an oil-in water emulsion. The dispersion is stable long enough to enable a dosage of the mouth wash to be dispensed, e.g., to the user, and the dispersion returns to the original state within two minutes when left at rest.

In one embodiment, the present invention is directed to Composition 1.0, a dual phase mouth wash composition comprising a hydrophobic phase, a hydrophilic phase, and a hydrotrope component. The hydrophobic and hydrophilic phases spontaneously separate following mixing and does not exhibit a microemulsion one hour following mixing. Mixing of the composition may occur in a container by hand, e.g., the container is shaken by hand for up to 1 minute, e.g., thirty seconds, or ten seconds at room temperature, and the composition is allowed to settle into distinct phases at room temperature.

Additional compositions of the present invention the following compositions:

1.1 Composition 1.0 wherein the hydrotrope component comprises a polyglycol, a polyhydric alcohol, or a mixture thereof;
1.2 Any of compositions 1.0-1.2 wherein the hydrotrope component comprises a diol;
1.3 Any of the preceding compositions wherein the hydrotrope component comprises a triol;
1.4 Any of the preceding compositions wherein the hydrotrope component comprises ethylene glycol, propylene glycol, glycerin, diethylene glycol, di-propylene glycol, tripropylene glycol, nexylene glycol, 1,3-butylene glycol, 1,4-butylene glycol, 1,2,6-hexanetriol, sorbitol, xylitol, and combinations thereof. e.g., from about 1% to about 70% by weight, from about 5% to about 60%, from about 10% to 50%, from about 15% to about 40% by weight of the composition;
1.5 Any of the preceding compositions wherein the hydrotrope component comprises glycerin and propylene glycol, e.g., in a weight ratio of from about 2:1 to about 1:2, e.g., about 1:1;
1.6 Any of the preceding compositions wherein the hydrotrope component comprises sorbitol;
1.7 Any of the preceding compositions wherein the hydrophobic phase comprises an oil selected from isopropyl myristate, mineral oil, and edible oils, such as olive oil, corn oil, coconut oil, soybean oil, and combinations thereof;
1.8 Any of the preceding compositions wherein the hydrophilic and/or hydrophobic phase comprise an active ingredient;
1.9 Any of the preceding compositions wherein the hydrophobic and/or the hydrophilic phase comprises an antibacterial agent;
1.10 Any one of the preceding compositions wherein the hydrophobic phase comprises a halogenated diphenyl ether;
1.11 Any one of the preceding compositions wherein the hydrophobic phase comprises triclosan;
1.12 Any of the preceding compositions wherein the hydrophobic phase comprises an essential oil;
1.13 Any of the preceding compositions wherein the hydrophilic phase comprises a polyvinylmethyl ether/maleic anhydride copolymer;
1.14 Any of the preceding compositions wherein the hydrophilic phase comprises a humectant, thickener, viscosity modifier, and combinations thereof;
1.5 Any of the preceding compositions comprising a flavoring, and/or coloring agents:

1.16 Any of the preceding compositions wherein the hydrophilic phase comprises a fluoride ion source selected from stannous fluoride, sodium fluoride, potassium fluoride, sodium monofluorophosphate, sodium fluorosilicate, ammonium fluorosilicate, amine fluoride, ammonium fluoride, and combinations thereof;

1.17 Any of the preceding compositions comprising from about 50 to about 5000 ppm fluoride ion, e.g., from about 100 to about 1000, from about 200 to about 500, or about 250 ppm fluoride ion;

1.18 Any of the preceding compositions comprising an antibacterial agent.

1.19 Any of the preceding compositions comprising an antibacterial agent selected from a halogenated diphenyl ether (trielosan), herbal extracts or essential oils (e.g. rosemary extract, thymol, menthol, eucalyptol, methyl salicylate), bisguanide antiseptics (e.g., chlorhexidine, alexidine or octenidine), phenolic antiseptics, hexetidine, povidone iodine, delmopinol, salifluor, metal ions (e.g., zinc salts, for example, zinc citrate), sanguinarine, propolis and oxygenating agents (e.g., hydrogen peroxide, buffered sodium peroxyborate or peroxycarbonate).

1.20 Any of the preceding compositions comprising triclosan;

1.21 Any of the preceding compositions comprising an antibacterial agent in an amount of 0.001% to about 1%, from about 0.01 to about 0.1%. or about 0.03 wt. % of the total composition weight.

1.22 Any of the preceding compositions comprising a chelating agent:

1.23 Any of the preceding compositions comprising a pyrophosphate salt, e.g., potassium pyrophosphate, sodium pyrophosphate, or a combination thereof;

1.24 Any of the preceding compositions wherein the hydrophilic phase comprises a tooth desensitizing agent;

1.25 Any of the preceding compositions comprising a tooth desensitizing agent selected from a potassium salt, capsaicin, eugenol, a strontium salt, a zinc salt, a chloride salt, or combinations thereof;

1.26 Any of the preceding compositions comprising from about 1% to about 90% by volume of the hydrophilic phase;

1.27 Any of the preceding compositions comprising from about 5% to about 90% by volume of the hydrophobic phase;

1.28 Any of the preceding compositions having about a 15:85 hydrophobic to hydrophilic weight ratio;

1.29 Any of the preceding compositions wherein the hydrophilic phase comprises the hydrotrope;

1.30 Any of the preceding compositions free or substantially free of a surfactant;

1.31 Any of the preceding compositions free or substantially free of a cationic surfactant;

The present invention also encompasses Method 2.0, a method to improve oral health comprising applying an effective amount of the oral composition of any of the embodiments under Compositions 1.0-1.31 to the oral cavity of a subject in need thereof, e.g. a method to 1. reduce or inhibit formation of dental caries,
2. reduce or inhibit demineralization and promote remineralization of the teeth,
3. reduce hypersensitivity of the teeth,
4. reduce or inhibit gingivitis,
5. inhibit microbial biofilm formation in the oral cavity.
6. treat and/or reduce plaque accumulation,
7. clean the teeth and/or oral cavity, and/or
8. Treat and/or reduce halitosis.

Other embodiments of the present invention will be apparent to one of skill in the art.

DETAILED DESCRIPTION OF THE INVENTION

As used herein, all measurement levels described herein are by weight of the total composition, unless otherwise indicated. Additionally, all references cited herein are hereby incorporated by reference in their entireties. However, in the event of a conflict between any definitions in the present disclosure and those in a cited reference, the present disclosure controls.

"Safe and effective amount" as used herein means a sufficient amount to treat the oral cavity, e.g., reduce plaque, gingivitis, and/or stain without harming the tissues and structures of the oral cavity.

As used herein, "cleaning" generally refers to the removal of contaminants, dirt, impurities, and/or extraneous matter on a target surface. For example, in the context of oral surfaces, where the surface is tooth enamel, the cleaning may remove at least some of a film or stain, such as plaque biofilm, pellicle or tartar.

The compositions of the present invention comprise a hydrophilic and a hydrophobic phase, and a hydrotrope component which when mixed form a temporary oil-in-water emulsion, which breaks down and separates back into the hydrophobic and hydrophilic phases within 5 seconds to one hour following mixing. It has been surprisingly determined that the separation of the hydrophilic and hydrophobic phases is complete, e.g., with no emulsion existing between the two phases. Without intending to be bound by theory, it is believed that the high HLB of the hydrotrope component allows for the complete separation of the two phases.

The hydrophobic phase of the composition of the present invention may contain any orally acceptable hydrophobic liquid, e.g., generally recognized as safe. Such materials are known in the art, and may include isopropyl myristate, liquid paraffin (mineral oil), edible oils such as olive oil, corn oil, coconut oil, soybean oil, and combinations thereof. A preferred hydrophobic phase comprises liquid paraffin, isopropyl myristate. Preferably, the hydrophobic phase has a HLB of from about 7 to 12, e.g., about 10.

The hydrophilic phase of the compositions of the present invention are aqueous based, e.g., having from about 40% to about 95% by weight water. Other useful materials may also include orally acceptable alcohols, humectants, or polymers. A humectant, on a pure humectant basis, generally includes about 10% to about 50% in one embodiment or about 15% to about 25% in another embodiment by weight of the mouth wash composition. The hydrophilic phase may optionally include one or more polymers, e.g., in the hydrophilic phase, such as polyvinylmethyl ether maleic acid copolymers, polysaccharides (e.g. cellulose derivatives, for example carboxymethyl cellulose, or polysaccharide gums, for example xanthan gum or carrageenan gum). The compositions of the present invention may contain an orally acceptable polyvinylmethylether/maleic anhydride (PVME/MA) copolymer. The PVME/MA copolymer is present from about 0.1% to about 20%, for example about 0.5% to about 10% by weight. Generally the methyl vinyl ether to maleic anhydride ratio in the copolymer is about 1:4 to about 4:1, and the copolymer has an average molecular weight of about 30,000 to about 1,000,000, for example about 30,000 to about 500,000.

Preferred PVME/MA copolymers include those under the GANTREZ brand from ISP (Wayne, N.J.). The PVME/MA copolymer may also act as an antibacterial enhancing agent if present in an antibacterial enhancing effective amount.

Hydrotropes are known in the art, and include compounds that solubilize hydrophobic compounds in aqueous solutions. Hydrotropes are low molecular weight amphiphilic compounds which resemble surfactants in as much as they have hydrophilic groups, and, in surfactant terms, what may be described as a low molecular weight hydrophobe. The hydrophilic group is may be attached to an organic moiety that is too short a group to confer true surface active properties. Hydrotropes useful in the present invention may include aromatic sulfonates, aromatic phosphate esters, di and polycarboxylates, polyglycols, and alcohols, including polyhydric alcohols. Hydrotropes useful in the present invention have a HLB value of from about 7 to about 18. Although any hydrotrope may be useful in the present invention (preferably GRAS), the hydrotrope may have a HLB value similar to that of the hydrophobic phase, and thus, the exact hydrotrope useful in the compositions will be dependent upon the composition of the hydrophobic phase. Preferably, the HLB of the coupling system is greater than the HLB of the hydrophobic phase, e.g., 10%, 15%, 20%, or 30% greater than the HLB of the hydrophobic phase. Methods of determining HLB is well known to those of skill in the art. The hydrotrope component in the present invention comprises one or more polyglycols and/or polyhydric alcohols, preferably a diol and/or a triol. Preferably, the coupling system comprises glycerine and propylene glycol. The exact ratio of glycerine and propylene glycol in the coupling system will depend on the desired HLB of the hydrotrope component of the present invention. As the hydrotrope lacks surfactant properties, the dispersion of the oil phase in the water is not thermodynamically stable, and an emulsion formed by mixing the two phases reverts back into separate and distinct phases immediately following mixing.

The compositions of the present invention incorporate one or more surfactants which are known in the art. Suitable surfactants include those which are reasonably stable throughout a wide pH range, for example, anionic, cationic, nonionic or zwitterionic surfactants. Preferred surfactants are nonionic surfactants. Preferably, the amount of surfactant in the compositions of the present invention is reduced to minimize the dispersion of the hydrophobic phase in the hydrophilic phase in the creation of emulsions which do not separate within about 2 minutes from mixing the phases. It has been surprisingly found that minimizing the surfactant content and the presence of hydrotropes allows for efficient separation of the two phases. In one embodiment of the present invention, the oral compositions are free, or substantially free of surfactants, especially anionic, cationic, and zwitterionic surfactants. Nonionic surfactants may be use in limited quantities in the present invention. Such nonionic surfactants may be defined as compounds produced by the condensation of alkylene oxide groups (hydrophilic in nature) with an organic hydrophobic compound which may be aliphatic or alkylaromatic in nature. Examples of suitable nonionic surfactants include, but are not limited to, the Pluronics, polyethylene oxide condensates of alkyl phenols, products derived from the condensation of ethylene oxide with the reaction product of propylene oxide and ethylene diamine, ethylene oxide condensates of aliphatic alcohols, long chain tertiary amine oxides, long chain tertiary phosphine oxides, long chain dialkyl sulfoxides and mixtures of such materials. The compositions of the present invention may contain from about 0.0001% to about 0.01% by weight of a surfactant.

The hydrophilic and/or hydrophobic phases may contain active ingredients, depending on the hydrophobicity of the active ingredient. Active ingredients include for example, fluoride, anti-bacterial active agents, anti-tartar agents, anti-caries agents, anti-inflammatory agents, anti-sensitivity agents, enzymes, nutrients, and the like. Actives useful herein are optionally present in the compositions of the present invention in safe and effective amounts that are sufficient to have the desired therapeutic or prophylactic effect in the human or lower animal subject to whom the active is administered, without undue adverse side effects (such as toxicity, irritation, or allergic response), commensurate with a reasonable risk/benefit ratio when used in the manner of this invention. The specific safe and effective amount of the active will vary with such factors as the particular condition being treated, the physical condition of the subject, the nature of concurrent therapy (if any), the specific active used, the specific dosage form, the carrier employed, and the desired dosage regimen.

Fluoride salts and fluoride ion sources, e.g., fluoride salts which may be soluble, are well known in the art and may be incorporated into the compositions of the present invention. Representative fluoride ion sources include, but are not limited to, stannous fluoride, sodium fluoride, potassium fluoride, sodium monofluorophosphate, sodium fluorosilicate, ammonium fluorosilicate, amine fluoride, ammonium fluoride, and combinations thereof. In certain embodiments the fluoride ion source includes stannous fluoride, sodium fluoride, amine fluorides, sodium monofluorophosphate, as well as mixtures thereof. In certain embodiments, the oral care composition of the invention may also contain a source of fluoride ions or fluorine-providing ingredient in amounts sufficient to supply about 50 to about 5000 ppm fluoride ion, e.g., from about 100 to about 1000, from about 200 to about 500, or about 250 ppm fluoride ion. Fluoride ion sources may be added to the compositions of the invention at a level of about 0.001 wt. % to about 10 wt. %, e.g., from about 0.003 wt. % to about 5 wt. %, 0.01 wt. % to about 1 wt., or about 0.05%; however, it is to be understood that the weights of fluoride salts to provide the appropriate level of fluoride ion will obviously vary based on the weight of the counter ion in the salt, and one of skill in the art may readily determine such amounts. A preferred fluoride salt may be sodium fluoride. Without intending to be bound by theory, the fluoride salt and/or fluoride ion source resides within the hydrophilic phase of the compositions of the present invention.

Antibacterial agents may be used in the compositions of the present invention, which may be present in amounts of about 0.001 to about 3.0% by weight of the compositions. A non-limiting list of useful additional oral care compounds includes non-ionic antibacterial agents, including phenolic and bisphenolic compounds, such as, halogenated diphenyl ethers, including triclosan (2,4,4'-trichloro-2'-hydroxy-diphenylether, triclocarban (3,4,4-trichlorocarbanilide), as well as 2-phenoxyethanol, benzoate esters, carbanilides, one or more basic amino acids, e.g., arginine, in free base or salt form, and combinations thereof. Such agents may be added in effective amounts, e.g., from about 1% to about 20% by weight based on the total weight of the composition, depending on the agent chosen. A halogenated diphenyl ether, such as triclosan, can be present in an amount of up to about 0.3% by weight of the oral composition, preferably around 0.03%.

The compositions of the present invention may incorporate one or more antisensitivity agents, e.g., potassium salts such as potassium nitrate, potassium bicarbonate, potassium chloride, potassium citrate, and potassium oxalate, capsaicin; eugenol; strontium salts, zinc salts; chloride salts and combinations thereof. Such agents may be added in effective amounts, e.g., from about 1% to about 20% by weight based on the total weight of the composition, depending on the agent chosen. The compositions of the present invention may also be used to treat hypersensitivity by blocking dentin tubules when applied to a tooth.

The compositions of the present invention may also include a tooth whitening or tooth bleaching composition, which are known in the art. Suitable whitening and bleaching compositions include peroxides, metal chlorites, persulfates. Peroxides include hydroperoxides, hydrogen peroxide, peroxides of alkali and alkaline earth metals, organic peroxy compounds, peroxy acids, and mixtures thereof. Peroxides of alkali and alkaline earth metals include lithium peroxide, potassium peroxide, sodium peroxide, magnesium peroxide, calcium peroxide, barium peroxide, and mixtures thereof. Other peroxides include perborate, urea peroxide, and mixtures thereof. Suitable metal chlorites may include calcium chlorite, barium chlorite, magnesium chlorite, lithium chlorite, sodium chlorite, and potassium chlorite. Such agents may be added in effective amounts, e.g., from about 1% to about 20% by weight based on the total weight of the composition, depending on the agent chosen.

The oral composition optionally comprises an anti-calculus composition, such as, for example, one or more of the anti-calculus compositions discussed in U.S. Pat. No. 5,292,526 to Gaffar, et al. In various embodiments, the anti-calculus composition includes one or more polyphosphates. The anti-calculus composition can include at least one wholly or partially neutralized alkali metal or ammonium tripolyphosphate or hexametaphosphate salt present in the oral composition at an effective anti-calculus amount. The anti-calculus active can also include at least one water soluble, linear, molecularly dehydrated polyphosphate salt effective in an anticalculus amount. The anti-calculus active can also include a mixture of potassium and sodium salts, at least one of which is present in an effective anti-calculus amount as a polyphosphate anti-calculus agent. The anti-calculus active agent can also contain an effective anticalculus amount of linear molecularly dehydrated polyphosphate salt anti-calculus agent present in a mixture of sodium and potassium salts. The ratio of potassium to sodium in the composition can be up to less than 3:1. The polyphosphate can be present in the oral composition in various amounts, such as an amount wherein the weight ratio of polyphosphate ion to anti-bacterial agent ranges from in excess of 0.72:1 to less than 4:1, or wherein the weight ratio of the anti-bacterial enhancing agent to the polyphosphate ion ranges from about 1:6 to about 2.7:1, or wherein the weight ratio of the anti-bacterial enhancing agent to the polyphosphate ranges from about 1:6 to about 2.7:1. Other useful anticalculus agents include polycarboxylate polymers and polyvinyl methyl ether/maleic anhydride (PVM/MA) copolymers, such as GANTREZ®.

The oral care compositions of the invention also may optionally include one or more chelating agents able to complex calcium found in the cell walls of the bacteria. Binding of this calcium weakens the bacterial cell wall and augments bacterial lysis. Another group of chelating agents which may be useful in the present invention is soluble pyrophosphate salts. Pyrophosphate salts used in the present compositions can be any of the alkali metal pyrophosphate salts. In certain embodiments, salts include tetra alkali metal pyrophosphate, dialkali metal diacid pyrophosphate, trialkali metal monoacid pyrophosphate and mixtures thereof, wherein the alkali metals are sodium or potassium. The salts are useful in both their hydrated and unhydrated forms. An effective amount of pyrophosphate salt useful in the present composition at least 0.1 wt. %, e.g., from about 0.5 wt. % to about 5 wt. %, about 1 wt. % to about 3 wt. %, or about 2%.

The oral care compositions of the invention may also optionally include one or more enzymes. Useful enzymes include any of the available proteases, glucanohydrolases, endoglycosidases, amylases, mutanases, lipases and mucinases or compatible mixtures thereof. In certain embodiments, the enzyme is a protease, dextranase, endoglycosidase and mutanase. In another embodiment, the enzyme is papain, endoglycosidase or a mixture of dextranase and mutanase. Additional enzymes suitable for use in the present invention are disclosed in U.S. Pat. No. 5,000,939 to Dring et al., U.S. Pat. No. 4,992,420; U.S. Pat. No. 4,355,022; U.S. Pat. No. 4,154,815; U.S. Pat. No. 4,058,595; U.S. Pat. No. 3,991,177; and U.S. Pat. No. 3,696,191 all incorporated herein by reference. An enzyme of a mixture of several compatible enzymes in the current invention constitutes about 0.002% to about 2.0% in one embodiment or about 0.05% to about 1.5% in another embodiment or in yet another embodiment about 0.1% to about 0.5%.

In preparing oral care compositions, it may be necessary to add some thickening material to provide a desirable consistency or to stabilize or enhance the performance of the formulation. In certain embodiments, the thickening agents are carboxyvinyl polymers, carrageenan, hydroxyethyl cellulose and water soluble salts of cellulose ethers such as sodium carboxymethyl cellulose and sodium carboxymethyl hydroxyethyl cellulose. Natural gums such as karaya, gum arabic, and gum tragacanth can also be incorporated. Colloidal magnesium aluminum silicate or finely divided silica can be used as component of the thickening composition to further improve the composition's texture. In certain embodiments, thickening agents in an amount of about 0.05% to about 10% by weight of the total composition are used, e.g., from about 0.1% to about 7%, from about 0.5% to about 5%, or about 1%, 2%, or less than about 2%. Other thickeners for use in oral compositions include natural and synthetic gums and colloids, such as carrageenan (Irish moss), xanthan gum, sodium carboxymethyl cellulose, starch, polyvinylpyrrolidone, hydroxyethylpropyl cellulose, hydroxybutyl methyl cellulose, hydroxypropylmethyl cellulose, and hydroxyethyl cellulose.

The compositions of the invention may also include one or more flavoring agents or coloring agents known by those of skill in the art. Flavoring agents which are used in the practice of the present invention include, but are not limited to, essential oils as well as various flavoring aldehydes, esters, alcohols, and similar materials. Examples of the essential oils include oils of spearmint, peppermint, wintergreen, sassafras, clove, sage, eucalyptus, marjoram, cinnamon, lemon, lime, grapefruit, and orange. Also useful are such chemicals as menthol, carvone, and anethole. Certain embodiments employ the oils of peppermint and spearmint. The flavoring agent is incorporated in the oral composition at a concentration of about 0.1 to about 5% by weight and about 0.5 to about 1.5% by weight.

The present invention provides for methods and processes of using the oral compositions of the present invention to clean oral surfaces and the oral cavity. Further, the oral compositions optionally treat and inhibit oral conditions, such as oral inflammatory conditions, dental plaque, and dental calculus. The oral compositions can be applied to the subject in any suitable manner known in the art. Generally, the composition is mixed or shaken for a period of time to mix the hydrophilic and hydrophobic phases. The mixed composition is then introduced into a user's oral cavity using a suitable applicator or delivery device, such as a brush, dental strip, film, syringe, or any other applicator or delivery device known in the art. The compositions can be used in prophylactic methods and processes to promote and maintain oral health, appearance, maintain systemic health and the like. The oral compositions can be repeatedly applied to the subject over a number of days according to a particular treatment schedule to treat and/or inhibit stain, plaque, calculus or tartar formation. Instructions setting forth the treatment schedule can be provided in commercial packaging with the product, as commercially prepared and stored.

The present invention is further illustrated through the following non-limiting example(s).

EXAMPLE I

Four mouth wash compositions are prepared with the following formulations:

|  | A | B | C | D | E |
|---|---|---|---|---|---|
| Hydrophobic Phase |  |  |  |  |  |
| Isopropyl myristate |  |  |  | 13 | 13 |
| Mineral Oil | 13 | 13 | 13 |  |  |
| Hydrophilic Phase |  |  |  |  |  |
| Water | 60 | 59.9 | 59.805 | 59.9 | 59.8 |
| Glycerin | 9 | 9 | 9 | 9 | 9 |
| Propylene Glycol | 9 | 9 | 9 | 9 | 9 |
| Sorbitol | 5 | 5 | 5 | 5 | 5 |
| Sodium pyrophosphate | 0.5 | 0.5 | 0.5 | 0.5 | 0.5 |
| Potassium pyrophosphate | 1.4 | 1.4 | 1.4 | 1.4 | 1.4 |
| PVM/MA copolymer | 0.3 | 0.3 | 0.3 | 0.3 | 0.3 |
| Sodium Fluoride | 0.05 | 0.05 | 0.05 | 0.05 | 0.05 |
| 30% Hydrogen peroxide solution |  |  | 0.1 | 0.1 | 0.1 |
| Flavor and colors | 1.745 | 1.75 | 1.745 | 1.75 | 1.75 |
| Surfactant | .005[1] | 0.1[2] | 0.1[1] |  | 0.1[3] |
|  | 100 | 100 | 100 |  | 100 |

[1]Nonionic surfactant
[2]Cationic surfactant
[3]Anionic surfactant

EXAMPLE 2

The four mouth wash compositions at room temperature of Example 1 are shaken by hand for 30 seconds to form an emulsion, and are allowed to rest for various amounts of time. No emulsion will be observed between the phases in Compositions A, and D 10 seconds at rest, while a emulsion will be observed in Compositions B, C and E after one hour at rest.

EXAMPLE 3

Compositions C, D and E are shaken for thirty seconds by hand per day for 90 days. At the end of the 90 days, it will be found that the peroxide activity of Composition C has decreased by 16%, the peroxide activity of Composition D only decreased by 5%., and the peroxide activity of E has decreased by 15%.

We claim:

1. A single-compartment dual phase mouth wash composition comprising:
   a hydrophobic phase;
   a hydrophilic phase comprising a fluoride ion source and an antibacterial agent; and
   a hydrotrope component,
   wherein hydrophobic and hydrophilic phases separate following mixing of the phases and does not contain an emulsion one hour following mixing, wherein the composition contains up to about 0.01% b weight of a surfactant.

2. The composition of claim 1 wherein the hydrotrope component comprises ethylene glycol, propylene glycol, glycerin, diethylene glycol, di-propylene glycol, tripropylene glycol, nexylene glycol, 1,3-butylene glycol, 1,4-butylene glycol, 1,2,6-hexanetriol, sorbitol, xylitol, or a combination thereof.

3. The composition of claim 1 wherein the hydrotrope component comprises sorbitol.

4. The composition of claim 1 wherein the hydrophobic phase comprises an oil selected from isopropyl myristate, mineral oil, an edible oil, and combinations thereof.

5. The composition of claim 1 comprising an active ingredient.

6. The composition claim 1, wherein the antibacterial agent is selected from a halogenated diphenyl ether, herbal extracts or essential oils, bisguanide antiseptics, phenolic antiseptics, hexetidine, povidone iodine, delmopinol, salifluor, metal ions, sanguinarine, propolis and oxygenating agents.

7. The composition of claim 1 comprising a halogenated diphenyl ether.

8. The composition of claim 1 comprising triclosan.

9. The composition of claim 1 wherein the hydrophobic phase comprises an essential oil.

10. The composition of claim 1 wherein the hydrophilic phase comprises a polyvinylmethylether/maleic anhydride copolymer.

11. The composition of claim 1 wherein the fluoride ion source is selected from stannous fluoride, sodium fluoride, potassium fluoride, sodium monofluorophosphate, sodium fluorosilicate, ammonium fluorosilicate, amine fluoride, amine fluoride, ammonium fluoride, and combinations thereof.

12. The composition of claim 1 comprising from about 50 to about 5000 ppm fluoride ion.

13. The composition of claim 1 comprising a chelating agent.

14. The composition claim 1 comprising a pyrophosphate salt.

15. The composition of claim 1 comprising a tooth desensitizing agent.

16. The composition of claim 1 comprising from about 1% to about 90% by volume of the hydrophilic phase.

17. The composition of claim 1 having about a 15:85 hydrophobic to hydrophilic weight ratio.

18. The composition of claim 1 wherein the hydrophilic phase comprises the hydrotrope component.

19. The composition of claim 6, wherein the herbal extract is selected from rosemary extract, thymol, menthol, eucalyptol and methyl salicylate; the halogenated diphenyl ether is triclosan; the bisguanide antiseptic is selected from chlorhexidine, alexidine and octenidine; the metal ion is a zinc salt; and the oxygenating agent is selected from hydrogen peroxide, buffered sodium peroxyborate and peroxycarbonate.

20. A method to improve oral health comprising applying an effective amount of the oral composition of claim 1 to the oral cavity of a subject in need thereof to:
- reduce or inhibit formation of dental caries,
- reduce or inhibit demineralization and promote remineralization of the teeth,
- reduce hypersensitivity of the teeth,
- reduce or inhibit gingivitis,
- inhibit microbial biofilm formation in the oral cavity,
- treat and/or reduce plaque accumulation, and/or
- clean the teeth and/or oral cavity and/or
- treat and/or reduce halitosis.

* * * * *